United States Patent [19]
Demuth et al.

[11] Patent Number: 5,289,381
[45] Date of Patent: Feb. 22, 1994

[54] METHOD AND APPARATUS FOR CONTINUOUSLY DETERMINING THE FINENESS OF FIBERS IN SLIVERS

[75] Inventors: Robert Demuth, Nurensdorf; Jurg Faas, Dinhard; Robert Moser, Winterthur, all of Switzerland

[73] Assignee: Maschinenfabrik Rieter AG, Winterthur, Switzerland

[21] Appl. No.: 17,407

[22] Filed: Feb. 11, 1993

Related U.S. Application Data

[63] Continuation of Ser. No. 622,012, Dec. 4, 1990, abandoned.

[30] Foreign Application Priority Data

Dec. 4, 1989 [CH] Switzerland ............... 04330/89

[51] Int. Cl.$^5$ ............................................ G06F 15/46
[52] U.S. Cl. ........................................ 364/470; 364/552
[58] Field of Search .............. 364/552, 470; 57/263, 57/264; 19/23, 239, 300, 301; 73/160

[56] References Cited

U.S. PATENT DOCUMENTS

| | | | |
|---|---|---|---|
| 3,854,330 | 12/1974 | Wildbolz | 73/160 |
| 4,296,409 | 10/1981 | Whitaker et al. | 364/580 X |
| 4,539,729 | 9/1985 | Meile et al. | 19/288 |
| 4,644,478 | 2/1987 | Stephens et al. | 364/185 X |
| 4,646,387 | 3/1987 | Oswald et al. | 19/0.23 |
| 4,758,968 | 7/1988 | Lord | 364/470 |
| 4,924,418 | 5/1990 | Bachman et al. | 364/550 |

FOREIGN PATENT DOCUMENTS

| | | |
|---|---|---|
| 765421 | 4/1971 | Belgium . |
| 78393 | 5/1983 | European Pat. Off. . |
| 0192835 | 9/1986 | European Pat. Off. . |
| 2323729 | 11/1973 | Fed. Rep. of Germany . |
| 2556747 | 6/1985 | France . |
| 629546 | 4/1982 | Switzerland . |
| 2036102 | 6/1980 | United Kingdom . |

*Primary Examiner*—Jerry Smith
*Assistant Examiner*—Jim Trammell
*Attorney, Agent, or Firm*—Sandler Greenblum & Bernstein

[57] ABSTRACT

A method and apparatus for converting measurement data pertaining to slivers and fibers originating from a continuous measurement that is dependent upon a plurality of parameters to calibration values. The plurality of parameters includes ambient, processing and measurement parameters. The parameters are converted and combined during processing. The resulting data relates only to individual property parameters and their changes per unit of time and are reduced to standard conditions with respect to ambient and processing parameters. The apparatus includes a plurality of sensors, a calibrating unit and a processing unit that function to continuously measure a quantity of material per length of the sliver and a variation in a fineness of the fiber per unit of time.

33 Claims, 5 Drawing Sheets

FIG. 4
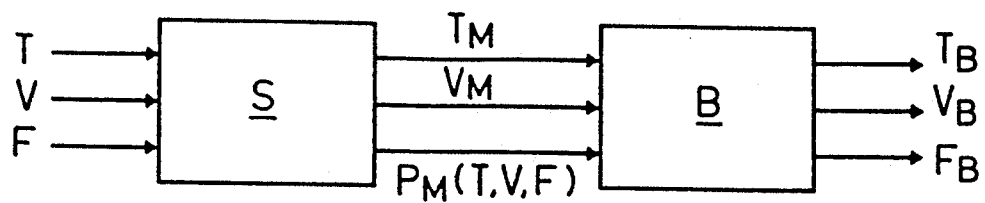
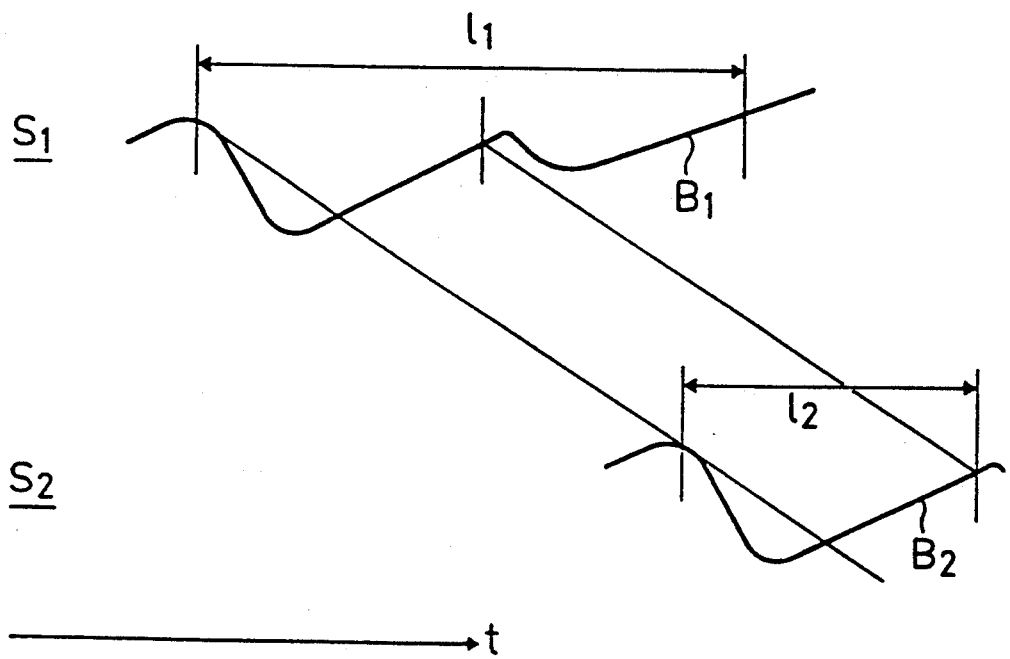
FIG. 5

METHOD AND APPARATUS FOR CONTINUOUSLY DETERMINING THE FINENESS OF FIBERS IN SLIVERS

This application is a continuation of application Ser. No. 07/622,012, filed Dec. 4, 1990, now abandoned.

FIELD OF THE INVENTION

The present invention is directed to the area of textile technology and specifically relates to an apparatus and method for measuring the fiber fineness in slivers, wherein changes in the fineness of a moving fiber that forms the sliver can be continuously determined.

DISCUSSION OF BACKGROUND AND RELEVANT INFORMATION

Blowroom and preparatory spinning facilities function to continuously produce slivers which, as far as possible, are not subject to any variations in any of their properties, and which correspond as far as possible to predetermined set-values. This problem can be optimally solved only by continuously monitoring and correcting the manufacturing process at different places in the manufacturing process sequence. Accordingly, data concerning the properties of the sliver at different places in the processing process must be made available.

The properties of a particular sliver prepared in a preparatory spinning facility depends upon a number of variables. These variables include the properties of the fibers, the nature and stage of the processing of the fiber and the ambient conditions. Thus, the properties of a specific sliver are determined by a set of parameter values.

Important sliver parameters include the origin of the fiber; the quantity of textile material per sliver unit length; the mutual position of the fibers that form the sliver; and the quantity, nature, size and form of foreign material and its distribution in the sliver. Important fiber parameters include the fineness and fineness distribution of the fibers forming the sliver; the length and length distribution of the fibers forming the sliver; the surface properties and forms of the fibers forming the sliver (i.e., degree of maturity); and, the fiber color. Important process parameters include the textile material or sliver material blend; the speed at which the sliver is formed; and, the tension of the sliver. Important ambient parameters include the humidity of the fibers and the environment; and, the temperature of the fibers and the environment.

Some of the above noted parameters must be kept constant per unit of time, as, for example, the ambient parameters. On the other hand, the staple length of the sliver is determined in several ways, such as, for example, using laboratory (i.e. static) methods, which are introduced as values into the process. The method under discussion here comprises a dynamic measuring method.

Two slivers have the same qualities if all the parameter values for both slivers are identical. Certain conclusions regarding the difference between two slivers, with respect to one parameter, can be made if all the other parameter values are the same, or, alternatively, if it is known whether a parameter value, is dependent upon another parameter value and if so, how. There are numerous standardized laboratory investigative methods for such comparison purposes. Such investigations are usually carried out under standardized ambient conditions and usually with standardized quantities and standardized arrangements of fibers in a static state. In this way, all of the above-mentioned processing, ambient and most of the sliver parameters are kept constant, so that it is possible to compare fibers, slivers and spun products.

The following measuring methods are known for continuously measuring the mass or fiber density of slivers:

European Patents 78,393 and 192,835 disclose measuring the mass of a sliver by mechanically compressing the sliver between two rollers. One of the rollers is driven and non-displaceable, while the second roller is entrained and is displaceable parallel to its own axis. The displaceable roller exerts a constant force on the sliver and is displaced from its rest position in accordance with the compressibility of the sliver. The deflection of the entrained roller is then measured. The deflection of the roller is mainly upon the fiber material and is a function of the quantity of fiber substance.

German Offenlegungsschrift 2,323,729 and Swiss Patent 629,546 disclose compressing a sliver in a trumpet in order to measure the density of the fiber. Dynamic pressure formed by air being squeezed out of the sliver is then measured. A variant of this measuring method comprises blowing an airstream having a constant pressure and constant flow through the sliver, perpendicularly to its direction of movement, and measuring a pressure drop over the sliver. In both cases, aerodynamic resistance of the sliver to the airstream is measured. The results of this type of measurement is primarily dependent upon the quantity of material, the fiber fineness, the fiber orientation in the sliver, the surface and shape of the fibers and the sliver speed.

Sliver measuring methods suitable for continuous investigations depend upon several parameters. However, in contrast to the non-continuous laboratory methods, it is not possible to eliminate the influence of several parameters by means of standard conditions (i.e., standardized preset conditions and/or invariability of some conditions over time). For example, ambient conditions and processing parameters may vary over time and at various points of the sliver production process in the blowroom and preparatory spinning facility. In addition, the sliver parameters and the fiber parameters may also vary. Since, however, the results of the continuous monitoring of the sliver properties can be used for instituting corrective actions and to activate alarms only if they can be reduced to individual parameters, it is important to find ways and means for breaking up the measurement results into individual and independent parameters. Since short-term and long-term fluctuations in the properties of slivers and fibers may lead to different corrective actions or alarms, it is important to separate these two types of fluctuations.

Practically all continuously obtained measurement results depend upon sliver humidity. These results cannot be compared with set values, unless they have previously been reduced to standard conditions. Controlling a flock feed and drafting process requires having data concerning material quantity on the sliver, which is produced by feeding and drafting, and this is necessary independently of the other fiber parameters. For example, controlling a bale opening and blenders requires having data relating to the fibers, irrespective of how much material the sliver under measurement contains at the time of measurement.

SUMMARY OF THE INVENTION

Accordingly, it is an object of the present invention to provide a method whereby measurements made at different places in a blowroom and preparatory spinning facility, using different measurement methods on slivers in different stages of treatment, can be processed so that one can obtain independent property parameters that are reduced to standard conditions or fluctuations of property parameters for the slivers and the fibers contained therein so that they can be directly compared with one another or with set values, and be utilized for monitoring and control purposes.

An advantage of the present invention is that long-term and short-term fluctuations may be separated, so that it is possible to provide data for different control purposes.

Another advantage of the present invention is that it is possible to provide an apparatus whereby two measurements can be obtained with respect to a sliver, so that one can get an indication of the quantity of material per unit length of the sliver and the fluctuations in the fineness of the fibers contained in the sliver. These two results are independent of the sliver speed and are reduced to standard ambient conditions According to an object of the present invention, a method is disclosed for continuously determining a fiber fineness and fluctuations thereof in slivers, comprising the steps of obtaining data signals from at least two different type sensors; and processing the signals from the sensors with one another, so as to determine specific property parameters which cannot be directly and specifically measured by analyzing the signals produced by another sensor.

According to the present invention, the signal processing step separates a data signal from an individual sensor that contains a plurality of property parameters from data signals of other sensors which contain only one property parameter. Furthermore, the data signal obtaining step uses a signal from a sensor that contains information concerning a plurality of property parameters with a signal from a sensor that contains information concerning one property parameter.

An advantage of the present invention is that the different type sensors can be positioned along a sliver path in a predetermined sequence, the sensors being spaced apart from each other by a predetermined distance. The signals produced by the sensors can be correlated to establish certain signals in response to property images between two consecutive sensors. The correlation step involves obtaining property images by measuring and storing measurement data from sliver increments of the sliver over a period of time, wherein when the determined property images of a sliver increment are compared the measured sliver increments are associated with one another in the event a preset maximum deviation value is undershot, and associated distances over time are utilized to associate measurement data of different type sensors. Further, the associated time values can be correlated with property images to form expected values that are used to measure sliver increments so as to form successive property images over a period of time for correlation purposes.

Another object of the present invention concerns an apparatus for continuously measuring a fiber fineness in a sliver. The apparatus has at least two sensors and a processing unit that forms fiber property parameters from signals produced from the sensors, at least one sensor being designed to produce a signal that is proportional to a sliver property measured by another sensor together with other sliver properties so that a non-directly measurable sliver property can be determined. In addition, the apparatus can include a calibrating unit.

An advantage of the apparatus constructed according to the present invention is that one sensor can measure a quantity of material per sliver length while another sensor measures the quantity of material per sliver length and the fiber fineness of said sliver.

Another advantage of the present invention is that one sensor can be used to measure a quantity of material per sliver length, the measurement being based upon a measuring of a mechanical resistance of the sliver to being compressed. Several alternative measuring systems can be used with present invention, One such example is to base the measurement upon a change of an electric field as the sliver passes through a capacitor arrangement. Alternatively, a quantity of material per sliver length and a fiber fineness can be measured by measuring a dynamic pressure that occurs as the sliver is compressed, either by a pair of rollers or by a trumpet.

BRIEF DESCRIPTION OF THE DRAWINGS

The foregoing and other objects, features and advantages of the present invention will be apparent from the following more particular description of a preferred embodiment of the invention, as illustrated in the accompanying drawings, in which reference characters refer to the same parts throughout the various views, and wherein:

FIG. 4 illustrates a graph showing the theory of the conditions imposed on observed parameters and measurements; and FIG. 5 illustrates a correlation of the sliver properties in the case of spaced sensors.

DESCRIPTION OF THE PREFERRED EMBODIMENTS

The present disclosure relates to subject matter contained in Swiss Application 04 330/89-0, which was filed on Dec. 4, 1989, and which is expressly incorporated herein by reference in its entirety.

A method according to the present invention is directed to measuring property parameters of a sliver and recovering them from the measurement result. It is assumed that the parameters to be measured are observable. That is, x (e.g., the measured value) is a function of p (e.g., parameters). If there is an inverse function, then p equals $f^{-1}(x)$. Thus, x equals $A \cdot p$, where A is a constant in matrix notation. If A is invertible, then p equals $A^{-1} \cdot x$. This is a non-linear relationship. Thus, the elements of A have to be determined.

In the present invention, the term "parameters" denotes properties which are present in the sliver and which are dependent upon the location, i.e., locally in the longitudinal direction of the sliver ( that is, not per unit of time) and which, when the sliver is in motion, are linked with time and can be treated as a function that depends on time.

Figure 1:
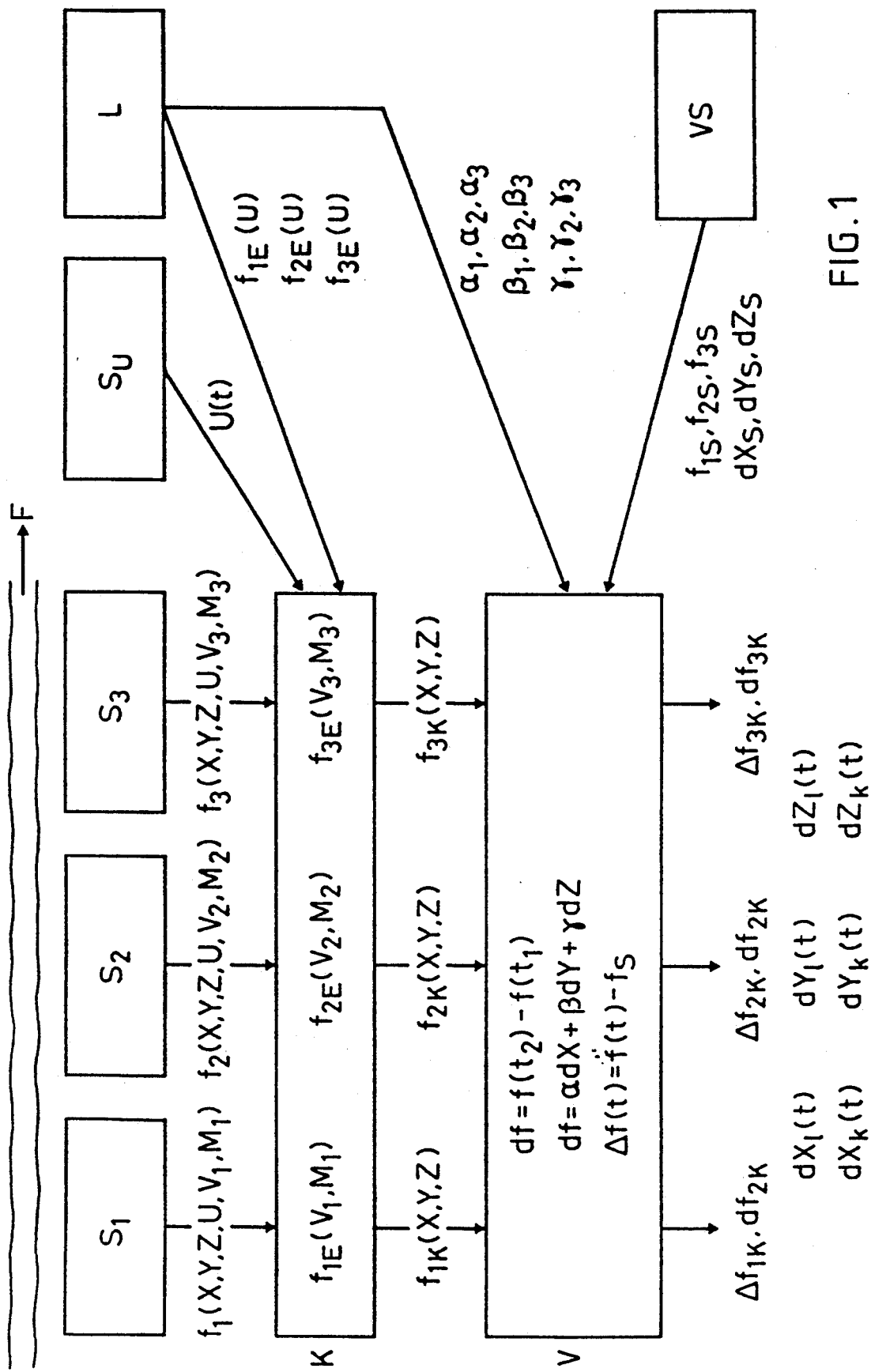
FIG. 1 illustrates a diagram of a sequence of a method according to the present invention.

FIG. 1 illustrates the sequence of the process of the present invention. Sliver moves from left to right at the top of the drawing, as indicated by arrow F, and is "scanned" by various sensors $S_1, S_2, S_3, \ldots S_u$. The sensors generate measurement signals $f_1, f_2, f_3, f_u$, which depend upon various parameters X, Y, Z, etc., of the sliver and fibers. Any number of sensors may be used, and the relationship between their output signals and the property parameters may differ. The measurement signals of the sensors are also dependent upon ambient parameters U, processing parameters V, and a specific sensor measuring method that is chosen, i.e. parameters $M_1, M_2, M_3$. The parameters X, Y, Z and U are in turn functions of time t, while the processing parameters V depend upon the measurement location.

The measurement signals $f_1, f_2, f_3, \ldots f_u$, are all fed to a calibrating unit K. The calibrating unit K also receives signals from sensor $S_u$, which comprises time-dependent values for the environment parameters U, such as, for example, values for air humidity and temperature. The calibrating unit K receives calibration functions or matrices $f_{1E}(U), f_{2E}(U), f_{3E}(U)$, etc., from a place at which static measurements are carried out under standardized conditions using laboratory methods, for determining the relationship between the measurements and ambient conditions U etc., and for the relationship between the measurements and ambient conditions U for the fiber material or fiber material blend currently being processed. The calibrating unit K in turn includes calibration functions $f_{1E}(M_1, V_1), f_{2E}(M_2, V_2), f_{3E}(M_3, V_3)$, etc., or corresponding mathematical algorithms, i.e., knowledge of the relationship between the measurement functions and measurement method and the processing parameters. The calibrating unit K uses all the calibration functions to determine calibrated measurement functions $f_{1K}(X,Y,Z), f_{2K}(X,Y,Z), f_{3K}(X,Y,Z)$, etc., which are only dependent upon the property parameters X, Y, Z, etc., and which are, in turn, functions of time. The calibrated measurement functions are reduced to standard conditions with respect to the ambient conditions and processing conditions. A typical function of the calibrating unit K, for example, eliminates the dependence of sliver speed from the measurement results, which is a factor involved in pneumatic measurement methods, in which the measurement signal is integrated over a variable time that is equivalent to a constant sliver length.

The calibrated measurement functions $f_{1K}, f_{2K}, f_{3K}$, etc., are fed to a processing unit. The processing unit contains mathematical algorithms, wherein the calibrated measurement functions are combined to obtain a result that is an independent property parameter and which is a function of time. Diverse variations are possible in this connection, from complex calibration functions to complex equation systems. The processing unit produces independent values for the property parameters, i.e., the actual functions X(t), Y(t), Z(t), etc., or, for other applications, the variations of the functions dX(t), dY(t), dZ(t), etc., over time. These values are then used for controlling and monitoring purposes.

In one embodiment of the processing unit, an example is described that employs three sensors and three property parameters. That is, an example is described in which absolute values of calibrated measurement functions and the variations of the individual property parameters with respect to time provide adequate information. A simple algorithm of a linear combination, which can be represented as matrix A, is employed in this processing unit. In a first approximation, it is assumed that the individual property parameters X, Y, Z, etc., are independent of one another and that their range of variations is small. The change in the measurement function over a short interval can thus be interpreted as the sum of the changes of all their determining parameters, which are in turn dependent on time. Thus, in a first approximation, the following applies to each calibrated measurement function:

$$df_K = \frac{\partial f_K}{\partial X} dX + \frac{\partial f_k}{\partial Y} dY + \frac{\partial f_k}{\partial Z} dz$$

If the individual derivatives of the parameters against time are considered to be approximately constant, the following applies:

$$df_k - \alpha dX + \beta dY + \gamma dZ$$

The factors $\alpha, \beta$ and $\gamma$ must be determined in the laboratory using static standardized conditions using the fiber material for processing. If three sensors are used that are dependent upon three property parameters, a linear equation system with three unknowns can be mathematically solved by the processing unit, according to the following equations:

$$df_{1K} - \alpha_1 dX + \beta_1 dY + \gamma_1 dZ$$

$$df_{2K} - \alpha_2 dX + \beta_2 dY + \gamma_2 dZ$$

$$df_{3K} - \alpha_3 dX + \beta_3 dY + \gamma_3 dZ$$

It should be noted that each of these equations are applied either for a specific time interval or for a specific time. If the sensors are positioned close together, then approximately the same time interval or same time can be taken for all the sensors. If, on the other hand, the sensors are positioned far apart, the time intervals, or times, must be selected to correspond to the sliver speed, so as to be equivalent to the passage of the same sliver portion. The resolution in each case is the same, and is dependent upon the length of the time interval, whereas the time between the first measurement and the availability of the measurement result increases in the case where the measuring stations are positioned far apart.

The following measuring system is cited as an example where the sensors are disposed "far" apart: $F_B$ is measured on a step roller at a card outlet and $F_{B+FF}$ is measured by an active-pneumatic trumpet at a sliver coiling inlet. This permits the sensors to be spaced from each other by several meters. In this arrangement, the sliver coiling system employs an autonomous drive.

Where measurements are carried out with sensors that are disposed far apart from each other, a method must be used for correlating the measurements. That is, despite the fact that the measuring stations are far apart, the sliver must be measured over the same sliver portion. This is achieved by using a correlation method. This method avoids measuring the distance that the sliver has to cover between the two measuring stations, which is advantageous when one deals with an on-line operation. The correlation stage is discussed below, in connection with FIG. 5.

Returning to the above equations, the only absolute values are the values of the calibrated measurement functions $f_{1K}, f_{2K}(t), f_{3K}(t)$, etc. Therefore, for a control operation that operates with absolute values, set values must be set for $f_{1S}$, $f_{2S}$, $f_{3S}$, etc. These values are then periodically compared, in the processing unit, with the values of the calibrated measurement functions over time, and processed to give corresponding differences.

The changes in property parameters can be averaged over shorter or longer intervals of time in the processing unit V. Short-term fluctuations $dX_k$, $dY_k$, $dZ_k$, etc., and long-term fluctuations $dX_l$, $dY_l$, $dZ_l$, etc., can then be determined from these average values. These fluctuations can be summed together and continuously compared with predetermined critical values $dX_S$, $dY_S$, $dZ_S$, etc. by a process control systems VS.

Variations of the above-described method can comprise using any required type of sensor arrangement with respect to the sensor sequence and mutual spacing. Referring to FIG. 1, sensors $S_1$, $S_2$, $S_3$, etc., can be given any desired permutations, resulting in a large number of possible on-line solutions. Variations are also possible in which the calibration procedure is delayed until after the processing or integrating calibrational parts thereof in the processing is performed. For example, the influence of humidity on the measurement results can be taken into account, not by reducing the measurement results to standard conditions, but rather, by adding an additional term, such as, an "interference term", to the equation of the linear processing combination. The interference term can also include other influences. It is noted that calibration measurements are required to determine the interference term.

The above-described method is given as a general example of the method according to the present invention. Using three or more sensors, whose measurement functions are dependent upon the same three or more property parameters, one can obtain variations of the three property parameters over time, and absolute calibrated values of the measurement functions. However, one cannot obtain absolute values of the individual property parameters. To obtain absolute values, the measurement functions of the sensors, after they are calibrated, can only depend upon one property parameter.

For important control parameters, such as, for example, the amount of material per sliver length, it is advantageous to use specific sensors which directly indicates a physical value under measurement and which do not need to determine the particular physical value using some indirect method, such as, for example, determining one parameter so that a second parameter can be calculated. On the other hand, less important parameters can be determined using indirect sensor methods. However, because each property parameter does not necessarily have a specific sensor that directly determines a parameter, it is often necessary to use sensor combinations to obtain desired property parameters.

Figure 2:
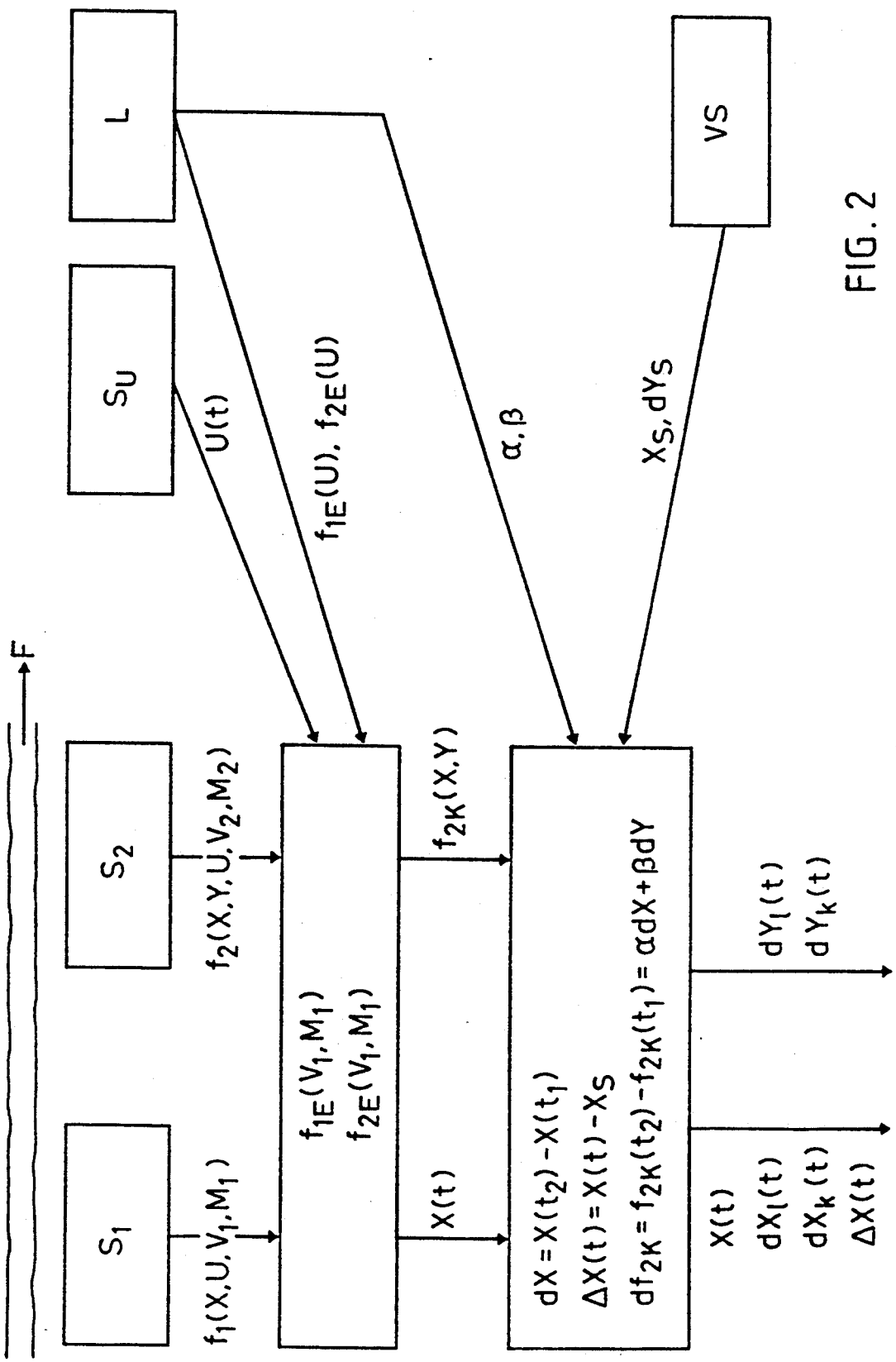
FIG. 2 illustrates the method diagram of FIG. 1 being applied to a specific application.

In FIG. 2, an example of the present invention is shown in which a specific sensor is employed in combination with a non-specific sensor. Sensor S comprises a specific sensor for obtaining data regarding property parameter X. Sensor $S_1$ obtains a measurement function, which is dependent upon property parameter X and on the ambient, processing and measurement parameters U, $V_1$, and $M_1$. Sensor $S_2$ comprises a non-specific sensor which obtains data in response to two property parameters X and Y. The calibrating unit K operates in the manner described above and produces two calibrated measurement functions $f_{1K}(X) = X(t)$ and $f_{2K}(X,Y)$. The processing unit V needs to only solve one equation and outputs functions X(t), dX(t), and dY(t), and their deviations from the corresponding values that are predetermined by the process control system. In this example, the measurement sequence is interchangeable, both in terms of time and space, and the distance between the two sensors $S_1$ and $S_2$ is unimportant, since the measurement chronology is linked by correlation, as will be discussed below with reference to FIG. 5. Reference should be made to Swiss Patent 629,546 for the measurement and handling of a speed parameter V.

A specific application of the present method is shown in FIG. 2. This example arises in the case of a combination of two property parameters; for example, a quantity of material per sliver length, and a fiber fineness. Assuming one disregards certain factors, various specific sensors are available for determining the quantity of material per sliver length. However, a specific sensor for determining a fiber fineness does not exist, although some sensors can be used as combined sensors for determining the quantity of material per sliver length and the fiber fineness, if, again, certain factors can be disregarded. Accordingly, in the presently discussed application, the quantity of material per sliver length is taken to be equal to property parameter X, while the fiber fineness would be equivalent to property parameter Y.

One example of a sensor that can be used for measuring the quantity of material per sliver length S1 is a mechanical sensor (i.e., a pair of rollers). A pneumatic sensor can be used as sensor $S_2$, for measuring the quantity of material together with the fiber fineness. The distance between the two sensors correspond to the local conditions of the process plant, and this also applies to the measuring station sequence, the measuring stations being interconnected by correlation. If it can be assumed that the property parameters do not vary from one sensor to another, and that the same interval of time can be taken for both measurements for determining the variation in fiber fineness per unit of time (as would be the case if there is a small distance between the sensors and a high sliver speed) correlation can be dispensed with. The calibrating unit operates as described above, so that the method used for calibration with respect to the sliver speed is integrated over constant sliver lengths. It is noted that two pieces of information are particularly important: (1) information concerning the long-term deviations of the quantity of material per sliver length, so that one can control the feeding and possibly the drafting processes; and, (2) the long-term fluctuations of the fiber fineness for monitoring the blowroom.

Figure 3A:
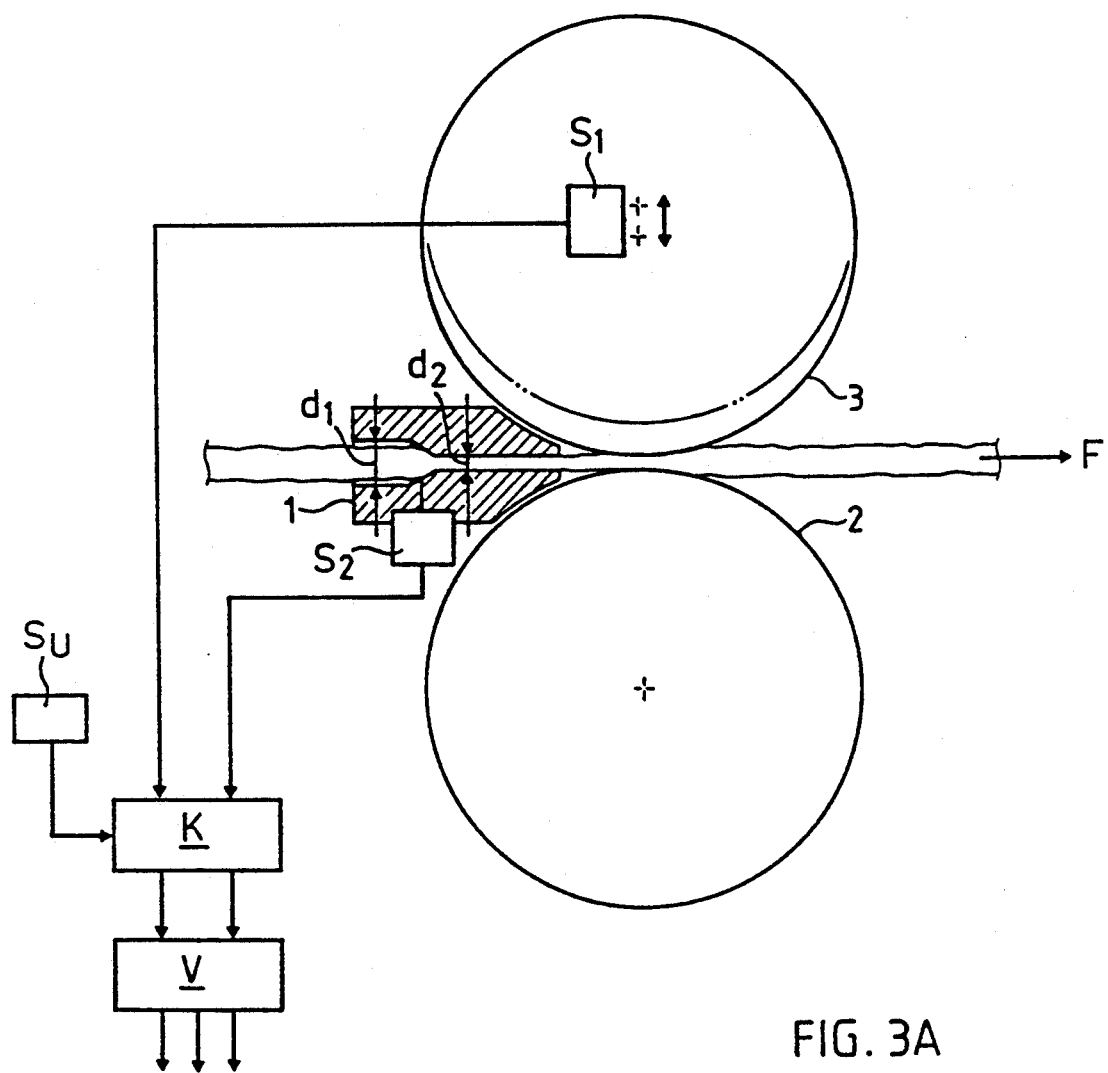
FIGS. 3A and 3B illustrate diagrams of a variation embodiment of the present invention according to the invention for performing the method shown in FIG. 2.

FIG. 3A illustrates an apparatus embodying the present invention for performing the method shown in FIG. 2, for determining the quantity of material per sliver length and fiber fineness fluctuations. The measuring sensors may be located at a number of places. For example, the sensors can be located at an inlet or outlet of a drafting frame or be installed at an outlet of a card or at a sliver coiler. In FIG. 3A, the sensors are disposed relatively close together in the sequence of a combination of a dependent sensor (e.g., a sliver trumpet 1) and a specific sensor (e.g., a step roller).

The fiber sliver passes through the trumpet 1, in which it is compressed from a diameter $d_1$ to a diameter $d_2$. The dynamic pressure arising from the compression is measured at a constriction point by sensor $S_2$. The trumpet 1 leads to a nip that is located between two rollers 2 and 3. Roller 2 comprises a driven, non-displaceable roller. Roller 3 comprises an entrained roller that is displaceable parallel to its longitudinal axis on the plane of the two roller longitudinal axes. When roller 3 is at rest, the distance between the two rollers 2 and 3 at its narrowest point is somewhat smaller than the diameter of the outlet aperture of the trumpet 1. Thus, the sliver is compressed between the two rollers 2 and 3. Since the sliver resists being compressed, roller 3 is displaced, and sensor $S_1$ measures the deflection of roller 3.

Two measurement functions are reduced in the calibrating unit K to standard ambient conditions. Further, the dependence of the pneumatic measurement upon the sliver speed is eliminated by integrating over a constant sliver length. The calibrating unit K is also responsible for including in the measuring results, by means of appropriate calibration values, the different tension states of the sliver before and after it is compressed in the trumpet 1, in the event that such an influence cannot be disregarded. As described above with respect to FIG. 2, the processing unit V processes the calibrated measurement functions. The processing unit V calculates the absolute value of the quantity of material per sliver length, the fluctuations per unit of time, and the fiber fineness fluctuations per unit of time. If the processing unit V is given appropriate set values, it will also deliver the deviations of the variables from these set values. The set value deviations of the quantity of material per sliver length are further used to control preceding feed devices and subsequent drafting processes. The deviations from the pre-set fiber fineness are used to correct the blend or to control an alarm in the event that an impermissible fluctuation occurs.

Figure 3B:
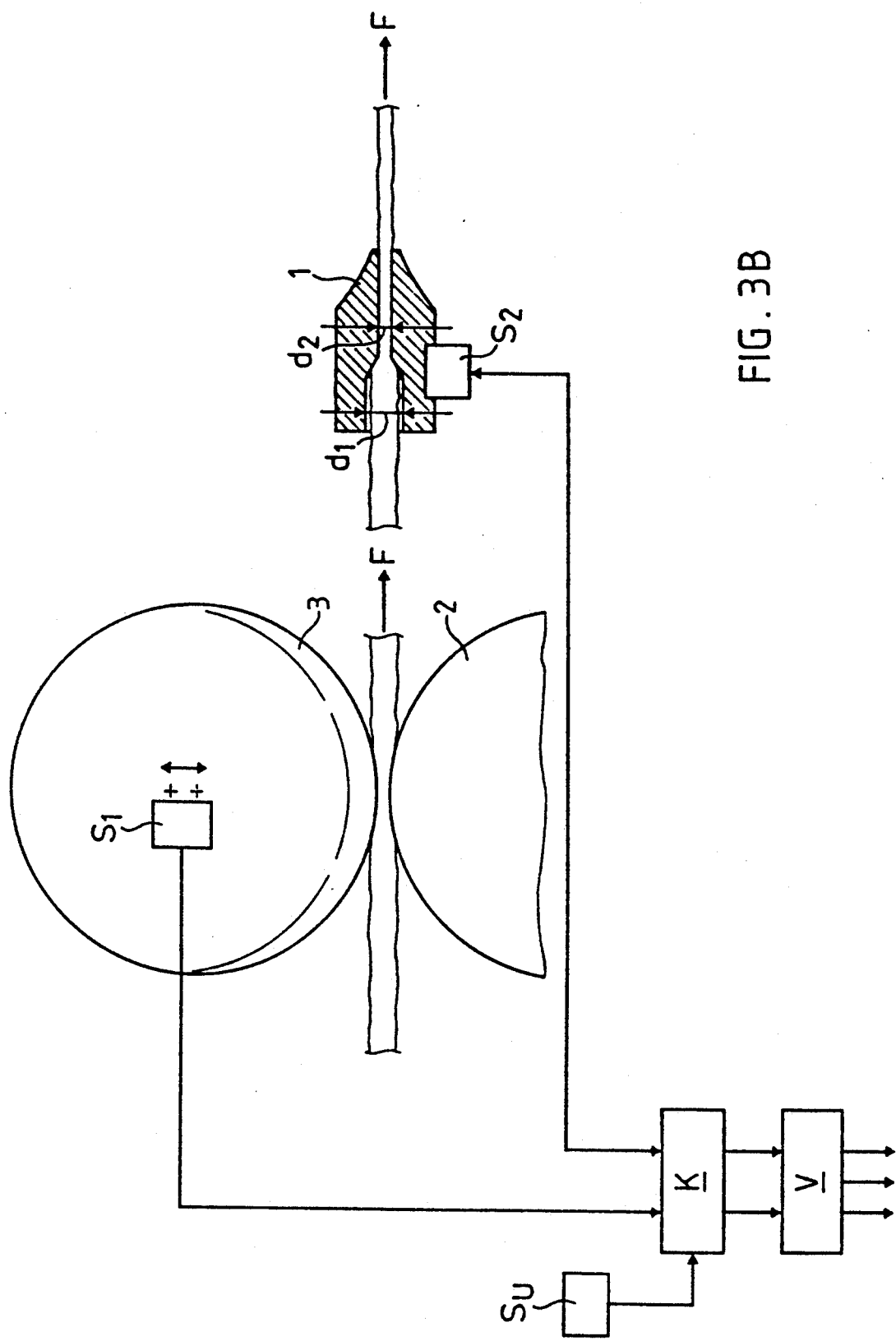

FIG. 3B illustrates an example in which the sliver trumpet 1 is positioned far away from the specific sensor $S_1$, which is the sensor associated with the step roller 3 near the sliver coiler. The sensor associated with the sliver trumpet 1 can be located at numerous places. The sliver passes sensor $S_1$ and sensor $S_2$, the distance between the two sensors being determined by a correlation calculation, so that sensor $S_2$ can, if required, be located in another position along the actual process operation without impairing the measurement of the fiber fineness. This increased flexibility facilitates the automation of a production plant.

FIG. 4 illustrates a measurement sequence, looking from an observer's viewpoint. As previously noted, the parameters must be observable. In FIG. 4, the observer plays an integral part of the method, rendering the parameters "visible". A sensor system S and an observer B are interconnected by measurement signals. Physical variables (such as, for example, yarn denier T, speed V, and fiber fineness F) are inputted to the sensor system S. The sensor system S produces measurement signals $T_M$, step roller deflection signals $V_M$ as a pulse/unit of time, and as differential pressures $P_M(T,V,F_{SLIVER})$ as determined by a pressure gauge at the sliver trumpet 1. These measurement signals are fed to the observer B, wherein they are converted to measurements of the physical inputs to the sensor system S, so as to produce denier signals $T_B$, speed signals $V_B$, and fiber fineness signals $F_B$. Note that an examination of FIG. 4 discloses that the physical variable F, which enters the measuring method as parameter $PM(T,V,F_{SLIVER})$ jointly with the other parameters, leaves the observer B as a separate parameter F.

FIG. 5 illustrates a diagram that shows the above-mentioned correlation, whereby the measurements of two spaced sensors can be combined in the manner described in the present invention. The properties of the sliver, which in a first approximation are taken as being time-independent, are recorded as functions of time by all the sensors when the sliver is moving. Each time increment corresponds to a sliver increment of a specific length. The same sliver increment passes the measuring zone of two spaced sensors at different times. The time difference between a sliver increment passing from one sensor $S_1$ to the second sensor $S_2$ is dependent upon the sliver speed and upon the distance between the two sensors. While both the order of magnitude of the sliver speed and the distance between the sensors are known, very small variations may occur, (for example, as a result of the passage of the sliver between the sensors $S_1$ and $S_2$). Thus, a correlation calculation is performed to ensure that the measurements of the two sensors to be accurately synchronized. The two sensors $S_1$ and $S_2$ measure certain property parameters of the sliver as a function of time. The measured values are fed to a correlation system via appropriate observers, and, in the described system, are converted to "property images" of sliver increments of constant length $l_1$ and $l_2$. "Property image" $B_1$ of the first sensor $S_1$ in the direction of the sliver transport are stored, while a "property image" $B_2$ of the second sensor $S_2$ are compared with the stored values. This comparison is performed with a correlation calculation, a threshold being preset for the minimal correlation quality required. Time increments of the corresponding "property images" correspond to identical sliver increments. Variations in the sliver properties in these increments can be fed to the combined evaluation system according to the present invention.

The continuous determination of the fineness of fibers in the slivers can successfully be obtained using two sensors if the influence of the fiber fineness, which results in a difference between two measurements, can be disregarded for the correlation. This presumes that the measurements are actually identical, which can be assumed for the first approximation for conventionally processed slivers. Another condition for using the correlation in the above sense is that the sliver must not be subjected to any changes between the two sensors.

A similarity measurement of the two signals is calculated by a correlation calculator. A correlation algorithm employs appropriate preset values and outline conditions, so that only the expected values need to be checked. As shown in FIG. 4, an observer "sees" signals which are determined by the fiber denier, by the fiber speed, or by the mass of the fiber in the sliver, and extracts from these signals sliver properties in accordance with a preset model. This model is expanded by a correlation algorithm which checks for a similarity between the two signals; that is, it determines whether a signal obtained at a specific time from a sensor located upstream in the process is the same as a signal obtained from a downstream sensor at a different time. The measuring sensors need not be identical, since the observer of FIG. 4 ensures that the physical variables are compared. If, for example, the yarn denier T is measured with the upstream sensor and a function f(T..) is determined by a later measuring sensor, the two measurements are determined by T and can thus be compared. Thus, it is unimportant if a "measurement result" lags behind the process sequence, i.e., because the required correlation is subsequently determined. The determination then forms the basis for a new expected value.

Thus, over a time increment $I_1$, a property image $B_1$ of successive fiber denier values is collected by sensor $S_1$ and the fiber denier values are simultaneously extracted and correlated at sensor $S_2$ from $f(T,V,F)$. A mean square variation, defined as an index, indicates excessive deviations, so that it can fairly well determine a signal difference $\delta(t)$. A standardized deviation index derived therefrom can then be used as a similarity index for the signals determined from T. The corresponding correlation coefficient is a value between $-1$ and $+1$, wherein $+1$ denotes a maximum similarity. The correlation coefficient is an index of a fixed position in time with respect to the compared signals. The correlation function, or the standardized auto-correlation function, applies for the shift between the two signals per unit of time. A defined expected value determines the number of samples and a confidence threshold determines the quality of the correlation. In addition, the processing is rendered dependent upon the quality of the correlation of the fiber fineness, which is extracted from the function $f(T,V,F)$.

Time variables associated with the correlated property images $B_1$, $B_2$ (i.e., the distance in time between two associated property images), can be used to form expected values. Thus, a downstream point in the measuring process can be expected to have measured properties in the sliver (which applies per unit of time), so that the measurement of the second property image and a successive correlation is unnecessary and is carried out only as a random sample.

It should be noted that the above-described apparatus is not able to separate the fiber fineness parameter from the surface nature parameter and the form of the fibers, and that fluctuations in the fiber material or blend, in soiling of the sliver or in the orientation of the fibers in the sliver, are interpreted as fluctuations in the quantity of material per sliver length.

While the present invention has been particularly shown and described with reference to the preferred embodiments thereof, it is understood by those skilled in the art that various alterations in form and detail may be made without departing from the spirit and scope of the invention as defined by the following claims. For instance, a sensor can measure a quantity of material per sliver length based upon the measuring of a change of an electric field as the sliver passes through a capacitor arrangement.

What is claimed is:

1. A method for continuously determining a fiber fineness and fluctuations thereof in slivers, comprising the steps of:
   obtaining data signals from at least two sensors that produce various type data signals;
   calibrating the various type data signals relative to a constant sliver length; and
   processing the various type data signals from said at least two sensors to form fiber property parameters, at least one sensor producing signals that are proportional to properties of said slivers which are measured in combination with other sliver properties by another sensor, such that a non-directly measurable sliver property can be determined.

2. The method of claim 1, wherein the step of processing the various type data signals comprises separating a data signal from an individual sensor that contains a plurality of property parameters from data signals of other sensors which obtain only one property parameter.

3. The method of claim 1, wherein the step of obtaining data signals comprises compiling a signal from a sensor that contains information concerning a plurality of property parameters with a signal from another sensor that contains information concerning one property parameter.

4. The method of claim 1, further comprising the step of positioning the at least two sensors along a sliver path in a predetermined sequence, the at least two sensors being spaced apart from each other by a predetermined distance.

5. The method of claim 4, further comprising the step of establishing a correlation between certain signals in response to property images between two consecutive sensors.

6. The method of claim 5, wherein the correlation establishing step comprises obtaining property images by measuring and storing measurement data from sliver increments of a sliver over a period of time, wherein when the determined property images of a sliver increment are compared, the measured sliver increments are associated with one another in the event a preset maximum deviation value is undershot, and associated distances over time are utilized to associate measurement data of different type 7. The method of claim 6, further comprising associating time values with correlated property images to form expected values.

8. The method of claim 7, wherein the expected values are used to measure sliver increments so as to form successive property images over a period of time for correlation purposes.

9. The method of claim 1, wherein said calibrating step comprises reducing measurement data for the purpose of standardizing conditions with respect to environment, processing and measurement parameters.

10. The method of claim 9, wherein the calibration step is carried out with appropriate calibration functions which are determined using at least continuous measurement methods or mathematical algorithms.

11. The method of claim 9, wherein the processing step comprises using at least non-continuous measurement functions or mathematical algorithms to determine appropriate calibration functions.

12. The method of claim 10, wherein the processing step comprises using a linear combination of derivatives of the measurement functions in accordance with individual property parameters.

13. The method of claim 12, further comprising the step of obtaining two measurements, one measurement being dependent only upon the quantity of material per sliver length, the second measurement being dependent upon the quantity of material per sliver length and on the fiber fineness.

14. An apparatus for continuously measuring a fiber fineness in a sliver, comprising:
   at least two sensors that produce various type data signals;
   a calibrating unit for calibrating said various type data signals relative to a constant sliver length; and
   a processing unit that forms fiber property parameters from said various type data signals produced by said at least two sensors, at least one sensor being designed to produce a signal that is proportional to a sliver property which is measured in combination with other sliver properties by another sensor, such that a non-directly measurable sliver property can be determined.

15. The apparatus of claim 14, wherein one sensor of said at least two sensors measures a quantity of material per sliver length and another sensor of said at least two sensors measures said quantity of material per sliver length and said fineness of said sliver.

16. The apparatus of claim 14, wherein one sensor of said at least two sensors measures a quantity of material per sliver length, said measurement being based upon a mechanical resistance of said sliver to be compressed.

17. The apparatus of claim 16, wherein said one sensor of said at least two sensors that measures said quantity of material per sliver length measures a deflection of one roller as said sliver is passed between a pair of roller, one of said rollers being movable, said sliver being compressed as said sliver is passed between said pair of rollers.

18. The apparatus of claim 17, wherein said one sensor of said at least two sensors that measures said quantity of material per sliver length comprises a pneumatic sensor that measures a dynamic pressure that occurs as said sliver is compressed in a trumpet.

19. The apparatus of claim 14, wherein one sensor of said at least two sensors measures a quantity of material per sliver length, said measurement being based upon a change of an electric field as said sliver passes through a capacitor arrangement.

20. The apparatus of claim 14, wherein one sensor of said at least two sensors measures a quantity of material per sliver length and a fiber fineness by measuring a dynamic pressure that occurs as said sliver is compressed.

21. The apparatus of claim 14, wherein said at least two sensors have mechanical and pneumatic measuring processes, said at least two sensors being postionable in a predetermined sequence along a movement direction of said sliver and being spaced apart from each other by a predetermined distance.

22. An apparatus for continuously measuring a fiber fineness in a sliver, comprising:
   a plurality of sensors;
   a processing unit for forming fiber property parameters based upon signals from said sensors; and
   a calibrating unit that calibrates said signals relative to a constant sliver length.

23. The apparatus of claim 22, wherein at least one sensor is designed to produce a non-directly measurable sliver property signal in response to a property signal produced by another sensor.

24. The apparatus of claim 22, wherein a sensor measures a quantity of material per sliver length based upon a deflection of one roller as said sliver is passed between a pair of rollers, one of said rollers being movable so that said sliver is compressed as said sliver is passed between said pair of rollers.

25. The apparatus of claim 22, wherein one of said plurality of sensors measures a quantity of material per sliver length, said measurement being based upon a change of an electric field as said sliver passes through a capacitor arrangement.

26. The apparatus of claim 22, wherein one of said plurality of sensors measures a quantity of material per sliver length and a fiber fineness by measuring a dynamic pressure that occurs as said sliver is compressed.

27. The apparatus of claim 22, wherein said calibrating unit further reduces measured functions to standard ambient conditions.

28. An apparatus for continuously measuring a fiber fineness in a sliver, comprising:
   a plurality of sensors which produce various type data signals;
   a processing unit that forms specific fiber property parameters pertaining to a finess of said fiber based upon said various type data signals produced by said plurality of sensors; and
   a calibrating unit that calibrates said various type data signals relative to a constant sliver length.

29. The apparatus of claim 28, wherein at least one sensor of said plurality of sensors is designed to produce a non-directly measurable sliver property signal in response to a property signal produced by another sensor of said plurality of sensors.

30. The apparatus of claim 28, wherein a sensor measures a quantity of material per sliver length based upon a deflection of one roller as said sliver is passed between a pair of rollers, one of said rollers being movable so that said sliver is compressed as said sliver is passed between said pair of rollers.

31. The apparatus of claim 28, wherein one sensor of said plurality of sensors measures a quantity of material per sliver length, said measurement being based upon a change of an electric field as said sliver passes through a capacitor arrangement.

32. The apparatus of claim 28, wherein one sensor of said plurality of sensors measures a quantity of material per sliver length and a fiber fineness by measuring a dynamic pressure that occurs as said sliver is compressed.

33. The apparatus of claim 28, wherein said calibrating unit further reduces measured functions to standard ambient conditions.

* * * * *